US006225312B1

(12) United States Patent
Feenstra et al.

(10) Patent No.: US 6,225,312 B1
(45) Date of Patent: May 1, 2001

(54) PIPERAZINE AND PIPERIDINE COMPOUNDS

(75) Inventors: Roelof Willem Feenstra; Cornelis Gerrit Kruse; Martinus Theodorus Maria Tulp; Wilma Kuipers; Stephen Kenneth Long, all of Weesp (NL)

(73) Assignee: Duphar International Research B.V. (NL)

( * ) Notice: Subject to any disclaimer, the term of this patent is extended or adjusted under 35 U.S.C. 154(b) by 0 days.

(21) Appl. No.: 09/155,608

(22) PCT Filed: Mar. 20, 1997

(86) PCT No.: PCT/EP97/01461

§ 371 Date: Mar. 4, 1999

§ 102(e) Date: Mar. 4, 1999

(87) PCT Pub. No.: WO97/36893

PCT Pub. Date: Oct. 9, 1997

(30) Foreign Application Priority Data

Mar. 29, 1996 (EP) .................................. 96200864

(51) Int. Cl.$^7$ ..................... C07D 405/04; C07D 411/04; C07D 413/04; C07D 401/04; A61K 31/496
(52) U.S. Cl. .................. 514/230.5; 514/252.13; 514/253.06; 514/254.09; 514/254.1; 514/254.11; 544/105; 544/362; 544/363; 544/369; 544/376; 544/377
(58) Field of Search ..................... 544/362, 363, 544/369, 376, 377, 105; 514/255, 254.1, 230.5, 252.13, 253.06, 254.09, 254.11

(56) References Cited

U.S. PATENT DOCUMENTS

| 4,415,572 | 11/1983 | Tominaga et al. | 424/250 |
|---|---|---|---|
| 4,772,604 | 9/1988 | Van Wijngaarden et al. | 514/252 |
| 4,782,061 | 11/1988 | Kruse et al. | 514/254 |
| 4,831,034 | 5/1989 | Barreau et al. | 514/255 |
| 4,874,770 | 10/1989 | Van Wijngaarden et al. | 514/326 |
| 5,153,206 | 10/1992 | Nagel | 514/326 |
| 5,240,942 | 8/1993 | Lavielle et al. | 514/314 |
| 5,242,933 | 9/1993 | Lavielle et al. | 514/338 |
| 5,250,544 | 10/1993 | Lavielle et al. | 514/319 |
| 5,260,317 | 11/1993 | Lavielle et al. | 514/314 |
| 5,278,185 | 1/1994 | Lavielle et al. | 514/428 |
| 5,292,761 | 3/1994 | Lavielle et al. | 514/357 |
| 5,294,619 | 3/1994 | Nagel | 514/299 |
| 5,424,313 | 6/1995 | Hartog et al. | 514/254 |
| 5,436,246 | 7/1995 | Bernotas et al. | 514/255 |
| 5,569,659 | 10/1996 | Reitz | 514/253 |

FOREIGN PATENT DOCUMENTS

| 0650964 | 5/1995 | (EP) . |
|---|---|---|
| WO 94/13659 | 6/1994 | (WO) . |
| WO 95/02592 | 1/1995 | (WO) . |

OTHER PUBLICATIONS

Chemical Abstracts, vol. 86, No. 5, Jan. 31, 1997, Abstract No. 29875a.
Chemical Abstracts, vol. 121, No. 15, Oct. 10, 1994, Abstract No. 179544x.

*Primary Examiner*—Mukund J. Shah
*Assistant Examiner*—Deepak R. Rao
(74) *Attorney, Agent, or Firm*—Finnegan, Henderson, Farabow, Garrett & Dunner, L.L.P.

(57) ABSTRACT

The invention relates to a group of new piperazine and piperidine compounds having interesting pharmacological properties. It has been found that compounds of formula (a) wherein A represents a heterocyclic group of 5–7 ring atoms wherein 1–3 heteroatoms from the group O, N and S are present; $R_1$ is hydrogen or fluoro; $R_2$ is $C_{1-4}$-alkyl, $C_{1-4}$-alkoxy or an oxo group, and p is 0, 1 or 2; Z represents carbon or nitrogen, and the dotted line is a single bond when Z is nitrogen, and a single or double bond when Z is carbon; $R_3$ and $R_4$ independently are hydrogen or $C_{1-4}$-alkyl; n has the value 1 or 2; $R_5$ is halogen, hydroxy, $C_{1-4}$-alkoxy or $C_{1-4}$-alkyl, and q is 0, 1, 2 or 3; Y is phenyl, furanyl or thienyl, which groups may be substituted with 1–3 substituents of the group hydroxy, halogen, $C_{1-4}$-alkoxy, $C_{1-4}$-alkyl, cyano, aminocarbonyl, mono- or di-$C_{1-4}$-alkylaminocarbonyl; and salts thereof show high affinity for both the dopamine $D_2$ and serotonin 5-$HT_{1A}$ receptors.

10 Claims, No Drawings

PIPERAZINE AND PIPERIDINE COMPOUNDS

This application is a 371 of PCT/EP97/01461 filed Mar. 20, 1997.

The invention relates to a group of new piperazine and piperidine compounds having interesting pharmacological properties.

It has been found that compounds of the formula (a)

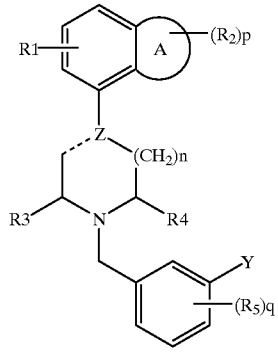

(a)

wherein

A represents a heterocyclic group of 5–7 ring atoms wherein 1–3 heteroatoms from the group O, N and S are present, $R_1$ is hydrogen or fluoro, $R_2$ is $C_{1-4}$-alkyl, $C_{1-4}$-alkoxy or an oxo group, and p is 0, 1 or 2

Z represents carbon or nitrogen, and the dotted line is a single bond when Z is nitrogen, and a single or double bond when Z is carbon, $R_3$ and $R_4$ independently are hydrogen or $C_{1-4}$-alkyl, n has the value 1 or 2

$R_5$ is halogen, hydroxy, $C_{1-4}$-alkoxy or $C_{1-4}$-alkyl, and q is 0, 1, 2 or 3

Y is phenyl, furanyl or thienyl, which groups may be substituted with 1–3 substituents of the group hydroxy, halogen, $C_{1-4}$-alkoxy, $C_{1-4}$-alkyl, cyano, aminocarbonyl, mono- or di-$C_{1-4}$-alkylaminocarbonyl, and salts thereof have interesting pharmacological properties.

Preferred compounds according to the invention are the compound formula (a) wherein A together with the phenyl group represents a group of the formula b–m

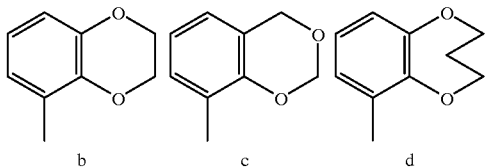

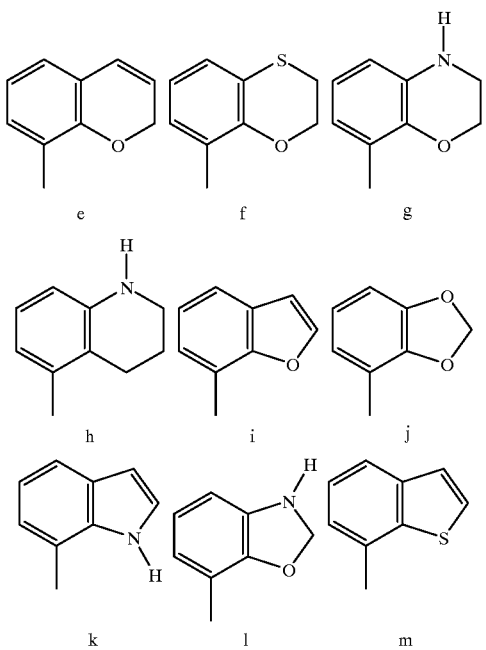

wherein $R_1$ and $(R_2)p$, n is 1, $R_3$, $R_4$, $(R_5)_q$, Y and Z have the above meaning, and salts thereof.

Especially preferred are the compounds of formula (a) wherein A together with the phenyl group represents a group of the formula (b), or a group of the formula (I) which is substituted in the hetero ring with an oxo group, and Y is phenyl which may be substituted as mentioned above and wherein n is 1, $R_3$ and $R_4$ are hydrogen, $R_5$ is hydroxy, methoxy or halogen, q is 0 or 1, Z is nitrogen, and salts thereof.

More especially preferred are the compounds of formula (a) wherein A together with the phenyl group is the group of formula (I) which is substituted in the heterorring with an oxo group, q is 0 and Y is phenyl, and salts thereof.

It is known from EP 0650964 that compounds of the formula

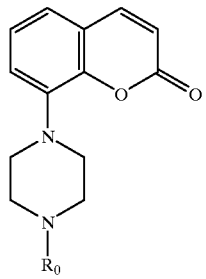

wherein $R_0$ is $C_{1-4}$-alkyl, which compounds can be substituted in the phenyl group and/or heterocyclic group and/or the piperazine group, act on the central nervous system by binding to 5-HT receptors. In particular these compounds bind to subtypes of the 5-HT-receptor, i.e. 5-$HT_{1A}$ and 5-$HT_{1D}$ receptors.

It has now surprisingly been found that the compounds according to the invention show high affinity for both the dopamine $D_2$ and serotonin 5-$HT_{1A}$ receptors (pKi range 7.0–9.5 for both receptor types). This combination is useful for the treatment of schizophrenia and other psychotic disorders and might allow for a more complete treatment of all disease symptoms (e.g. positive symptoms, negative symptoms and cognitive deficits).

The compounds show varying activities as either partial agonists or antagonists at dopamine $D_2$-, $D_3$- and $D_4$-receptors. Some compounds show agonist-like effects at dopamine receptors, however they potently antagonize apomorphine-induced climbing behaviour in mice ($ED_{50}$ values<1 mg/kg p.o). The compounds show varying activity as 5-$HT_{1A}$ receptor agonists and induce aspects of the serotinin behavioural syndrome to differing intensities.

The compounds are active in therapeutic models sensitive to clinically relevant antipsychotics (e.g. the conditioned avoidance response; Van der Heyden & Bradford, Behav. Brain Res., 1988, 31:61–67), antidepressants (e.g. differential reinforcement of low rate responses; van Hest et al., Psychopharmacology, 1992, 107:474–479) and anxiolytics (e.g. suppresion of stress-induced vocalization; van der Poel et al., Psychopharmacology, 1989, 97: 147–148).

In contrast to clinically relevant dopamine $D_2$ receptor antagonists the described compounds have a low propensity to induce catalepsy in rodents and as such are likely to induce less extrapyramidal side effects than existing antipsychotic agents.

The 5-$HT_{1A}$ receptor agonism inherent in these compounds may be responsible for the reduced tendency to induce extrapyramidal effects and the therapeutic effects observed in behavioural models sensitive to either antidepressants or anxiolytics.

The compounds are likely to be of value for the treatment of affections or diseases of the central nervous system caused by disturbances in either the dopaminergic or serotinergic systems, for example: Parkinson's disease, aggression, anxiety disorders, autism, vertigo, depression, disturbances of cognition or memory and in particular schizophrenia and other psychotic disorders.

Suitable acids with which the compounds can form pharmaceutically acceptable acid addition salts are for example hydrochloric acid, sulphuric acid, phosphoric acid, nitric acid, and organic acids such as citric acid, fumaric acid, maleic acid, tartaric acid, acetic acid, benzoic acid, p-toluene sulphonic acid, methanesulphonic acid and naphtalene-sulphonic acid.

The compounds of the invention can be brought into forms for administration by means of usual processes using auxiliary substances such as liquid and solid carrier materials.

The compounds of the invention can be obtained according to a number of methods (A to E) which are described below. The piperazines, homopiperazines and piperidines used in these methods are indicated as I-H to XIX-H, wherein I to XIX represent the following groups:

FIG. A1

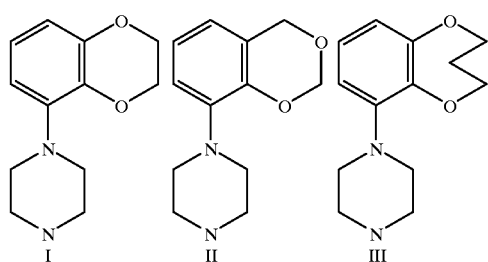

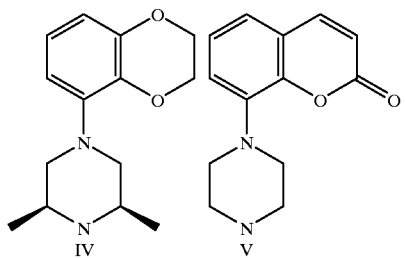

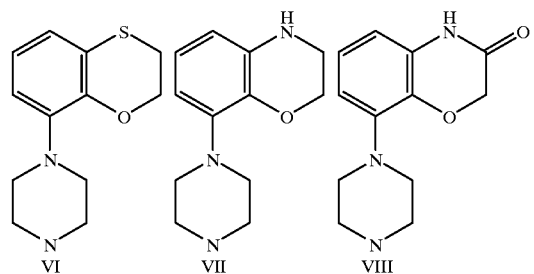

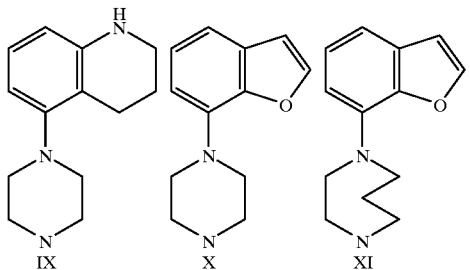

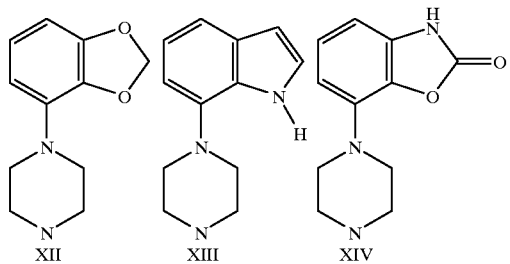

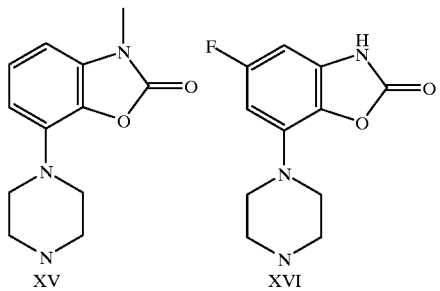

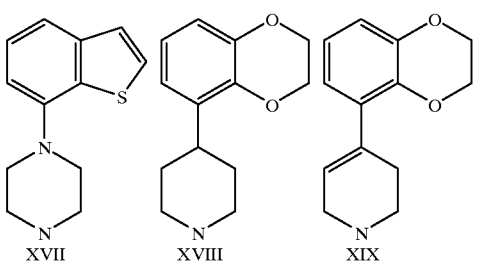

The synthesis of the piperidines XVIII-H and XIX-H (FIG. A1) used in the preparations of the compounds of the invention is analogous to the procedure described in WO 94-GB 1507.

The synthesis of the piperazines (FIG. A1) used in the preparations of the compounds of the invention are described in EP0189612, with the exception of XI-H, XIII-H and XV-H (vide infra).

The homopiperazine XI-H and piperazines XIII-H and XV-H are new and their preparations are given below (schemes A.i–A.iii).

Preparation XI-H:

scheme A.i

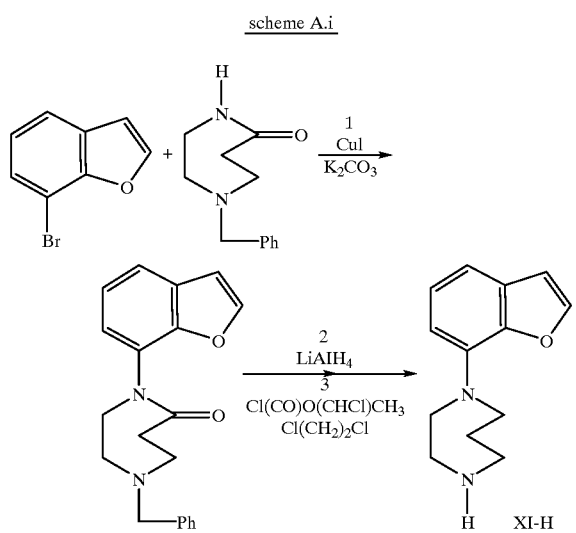

Preparation XIII-H:

scheme A.ii

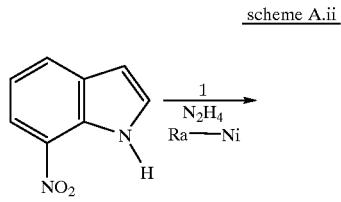

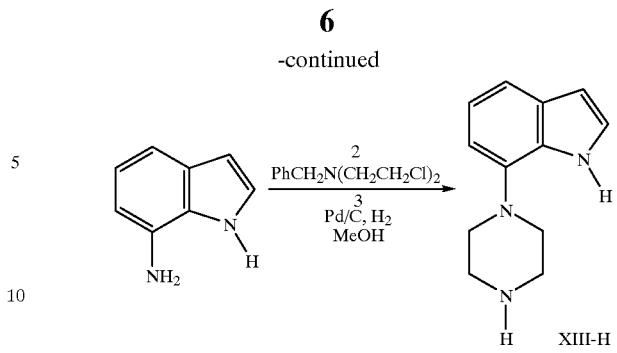

Steps 1 to 3 (scheme A.ii):
7-nitro-indole has been described by S. M. Parmerter et al., J. Am. Chem. Soc. 80, (1958), 4621–2, Steps 1,2 and 3 were carried out similarly to the syntheses described in European patent publication no. 0650964.

Preparation XV-H:

scheme A.iii

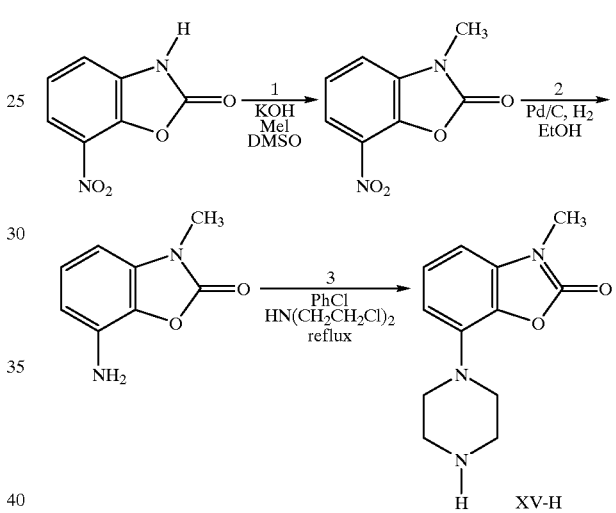

Step 1 to 3 of Scheme A.i and step 1 of the scheme A.iii are described in detail in the Examples, and the procedures of step 2 and 3 of Scheme A.iii are similar to those described in EP0189612.

The H-atom of the N—H moiety of compounds I-H to XIX-H can be replaced by group Q in five different chemical ways (A, B, C, D and E, vide infra), eventually leading to the compounds of the invention. In FIG. A2 the meanings of Q1 to Q34 are given.

Groups Q
FIG. A2

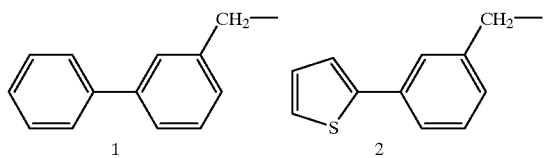

-continued
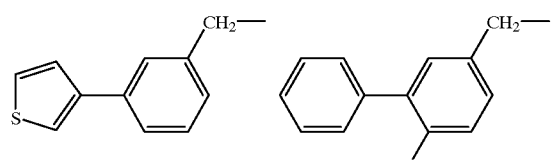
3, 4
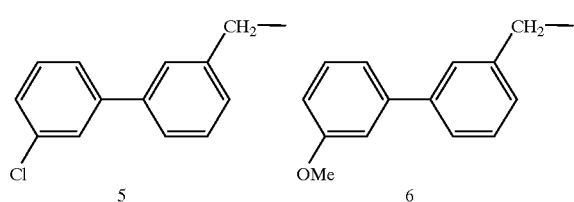
5, 6
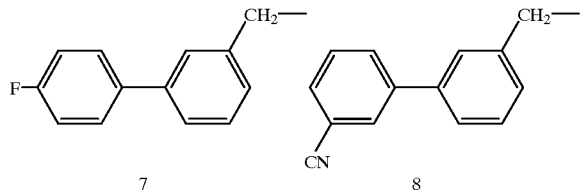
7, 8
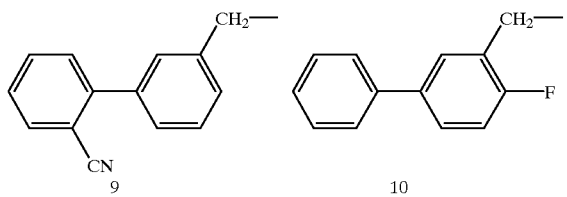
9, 10
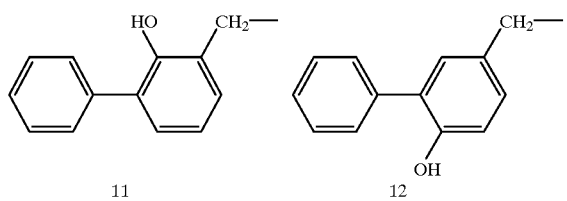
11, 12
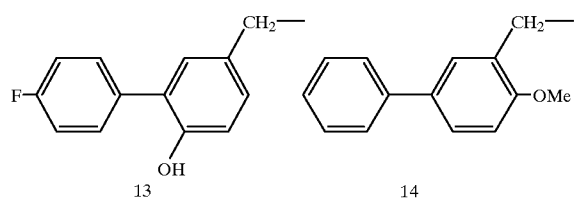
13, 14
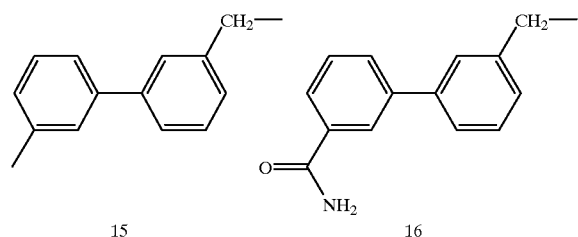
15, 16
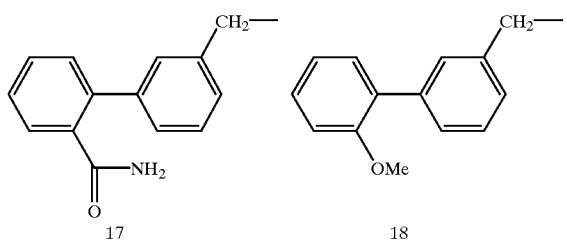
17, 18

-continued
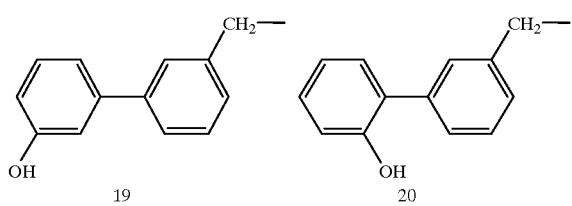
19    20
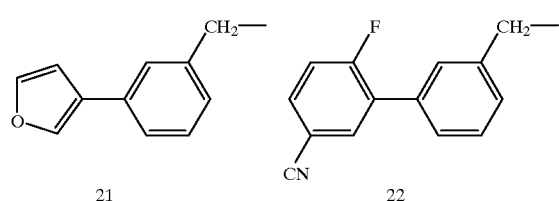
21    22
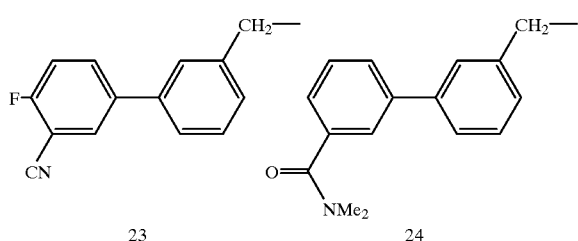
23    24
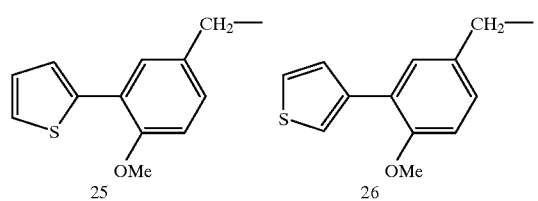
25    26
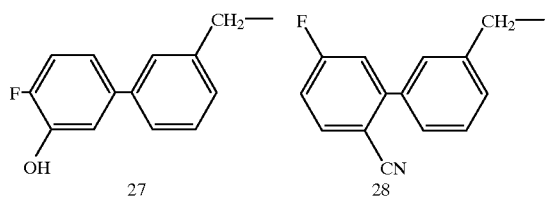
27    28
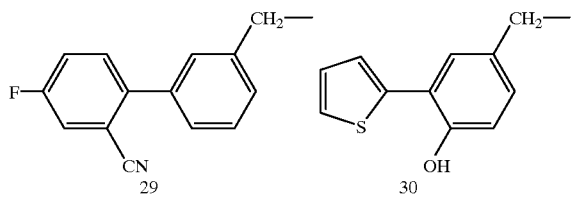
29    30
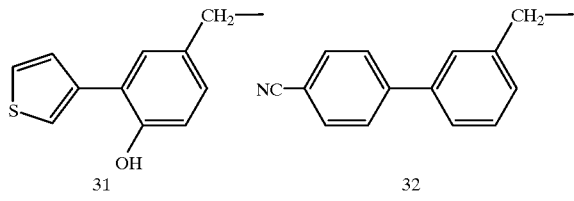
31    32
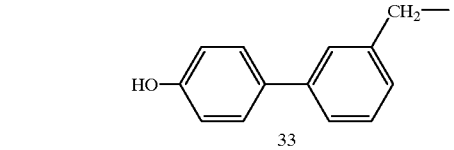
33

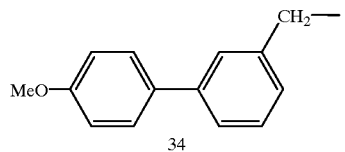

34

Synthesis Route A

The compounds A1–A14 and A16–A28 were prepared to the synthesis depicted in scheme A1 (vide infra). A piperazine (I-H to VI-H and VIII-H to XVII-H) was reacted with Q-X (X=Cl, Br, OMs) in acetonitrile with Et(i-Pr)$_2$N acting as a base, in some cases KI were added. Et$_3$N can be used instead of Et(iPr)$_2$N.

scheme A1

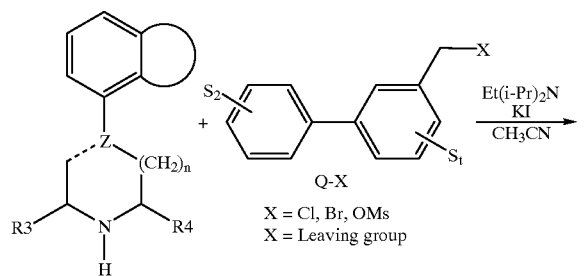

----- = single or double bond

The following synthesis routes B to E are not restricted to the preparation of piperazines, but can also be used for the preparation of piperidines.

Synthesis Route B

The compounds can also be prepared according to the synthesis depicted in scheme B1 (vide infra). Piperazine I-H was reacted with 2-phenyl-phenol and formaldehyde in EtOH.

scheme B1

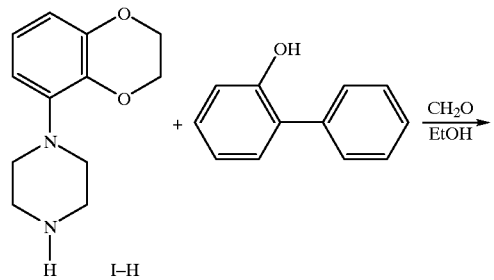

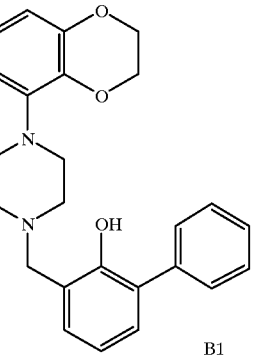

Synthesis Route C

The compounds C1–C4 were prepared according to the synthesis depicted in scheme C1 (vide infra). Phenylpiperazines were reacted with several meta-subsituted phenylbenzoic acid chlorides to yield the corresponding amides. The amides were subsequently reduced to compounds C1–C4 with the aid of LiAlH$_4$.

scheme C1

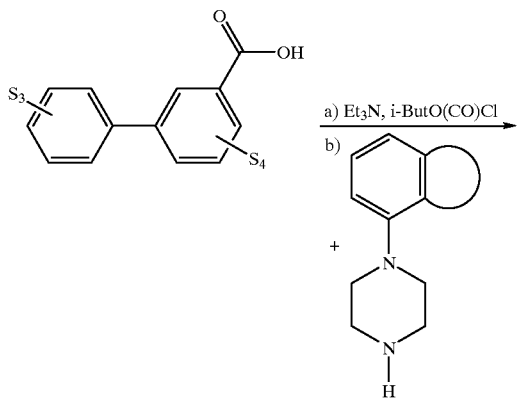

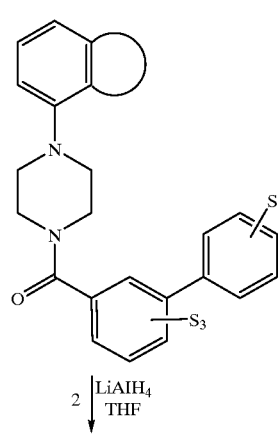

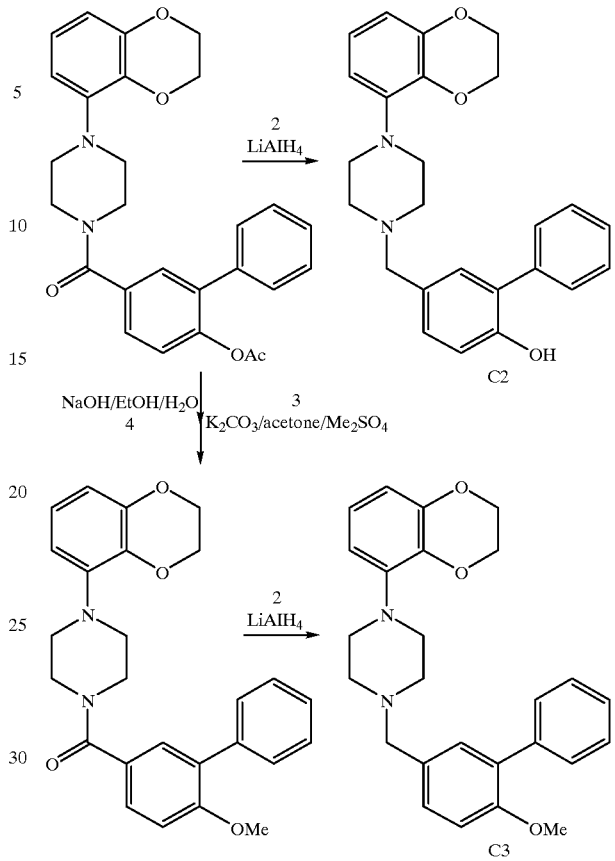

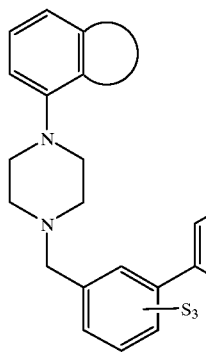

Compounds C2 and C3 were prepared as depicted in scheme C2.

Synthesis Route D

The compounds D1–D18 and D21–D23 were prepared according to the synthesis depicted in scheme D1 (vide infra). An arylboronic acid was reacted with an aromatic bromide under basic conditions in the presence of a catalytic amount of Pd(PPh$_3$)$_4$. This so-called "Suzuki" reaction yields the C—C coupled endproducts D.

scheme C2

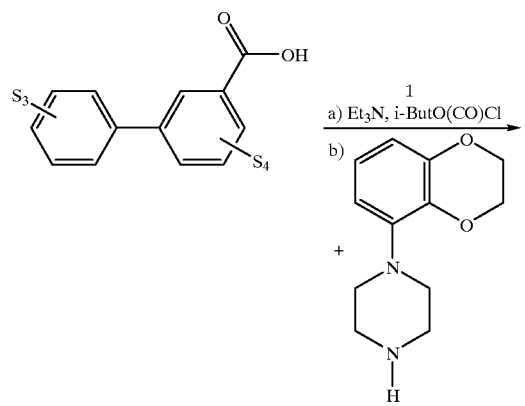

scheme D1

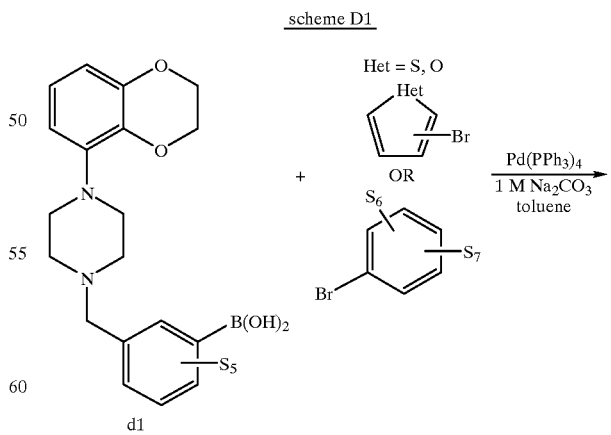

-continued

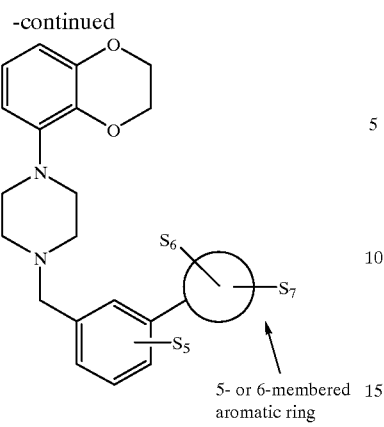

5- or 6-membered aromatic ring

The compounds D19 and D20 were prepared according to a modified synthesis which is depicted in scheme D2:

scheme D2

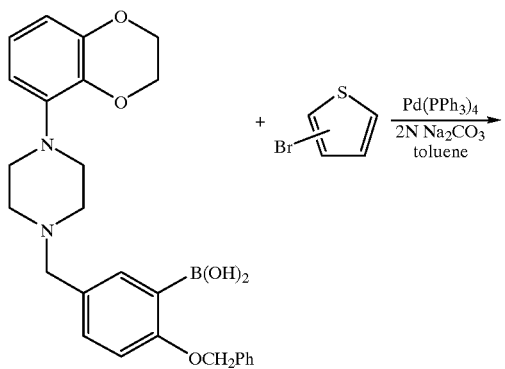

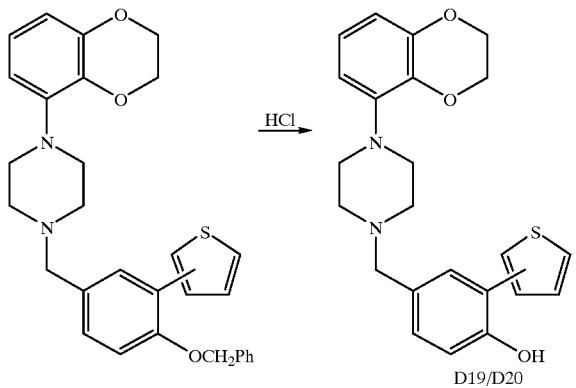

D19/D20

After the above described Suzuki reaction has taken place, an additional hydrolysis step removes the protective benzyl group by standard procedures (e.g. hot concentrated HCl), for an example see also procedure E2 (scheme E2).

Synthesis Route E

The compounds E2 and E3 were prepared according to the synthesis depicted in scheme E1. Though the intermediates are different, the same Suzuki reaction is applied here as the one described in synthesis route D.

scheme E1

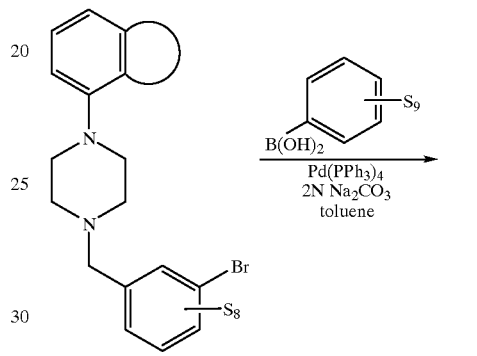

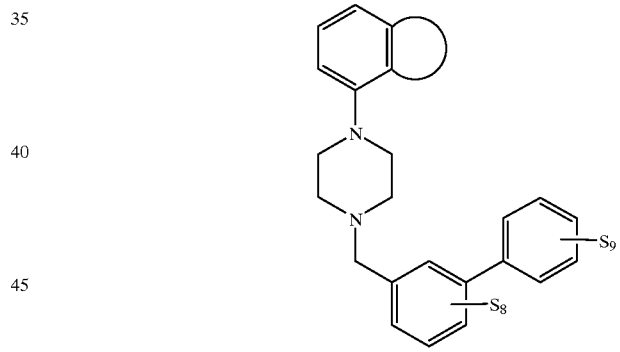

The compound E1 was prepared according to a modified synthesis which is depicted in scheme E2. An additional step to the synthesis depicted in scheme E1, was the hydrolysis of the protective benzyl group.

scheme E2

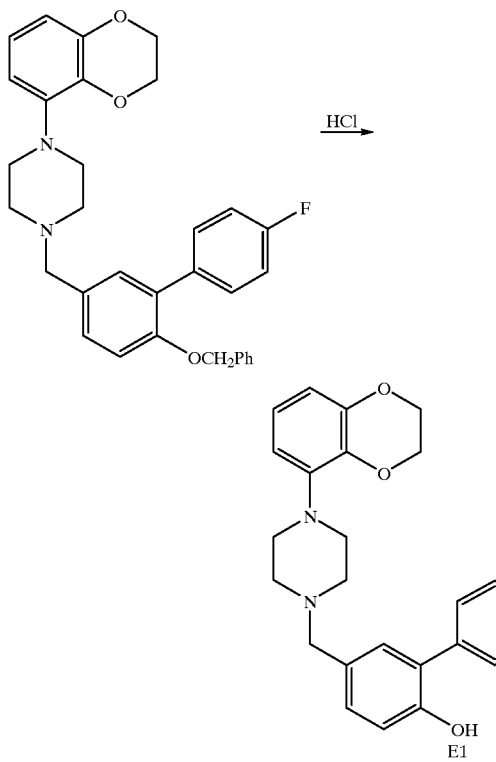

The preparation of the compounds of formula (a) and of a number of intermediate compounds will now be described in detail in the following Examples.

EXAMPLE 1

Procedure A1 (Scheme A1)

1.0 g (4.3 mmol) of piperazine III-H and 1.2 g (4.7 mmol) of Q1-Br were added to 20 ml of $CH_3CN$, after which 0.52 g (5.1 mmol) of $Et_3N$ and a small amount of KI were added. The reaction mixture was stirred and allowed to reflux for 16 hrs under a nitrogen atmosphere. After cooling of the mixture, the solvent was removed in vacuo, leaving a residue which was dissolved in $CH_2Cl_2$ and subsequently washed with 0.5 N NaOH and brine (2x). The organic fraction was dried on $MgSO_4$. After removal of the drying agent the solvent was removed in vacuo leaving a residue. The latter yielded after flash column chromatography ($SiO_2$, eluent: $CH_2Cl_2$/MeOH 99/1) compound A11 (free base, see table A1)). Subsequently the residue was dissolved in ether to which one equivalent of 1N HCl/EtOH was added. Precipitation took place and yielded 0.98 g (2.3 mmol, 52%) of pure A11.HCl m.p.: 228–30° C. $^1$H-NMR($CDCl_3$, δ): 2.18 (m, 2H), 3.09(broad, 2H), 3.3–3.7(broad cluster, 6H), 4.21(m, 4H), 4.30(s, 2H), 6.59(dd, J=1 and 8 Hz, 1H), 6.71(dd, J=1 and 8 Hz, 1H), 6.82(t, J=8 Hz, 1H), 7.37(m, 1H), 7.47(m, 2H), 7.53(t, J=8 Hz, 1H), 7.62–7.74(cluster, 4H), 7.90(t, J=2 Hz, 1H), 12.9(broad, 1H).

According to the synthesis given above, the compounds A1–A14 and A16–A28 were prepared in a similar way, for a summary see table A1. Compound A15 was prepared from compound A14 by reduction with $LiAlH_4$/THF similarly to procedure A5 (vide infra, the reduction of A14 was carried out at reflux temperature instead of room temperature).

TABLE A1

| compound nr | piperazine | Q | X | SALT | melting point ° C. | |
|---|---|---|---|---|---|---|
| A1 | I | 1 | Br | HCl | 221–3 | |
| A2 | XIV | 1 | Br | HCl | 304–6 | |
| A3 | IX | 1 | Br | 2HCl | 258–60 | d |
| A4 | X | 1 | Br | 2HCl | 218–9 | |
| A5 | XI | 1 | Br | 2HCl | 188–9 | |
| A6 | XIV | 2 | OMs | HCl | 284–6 | d |
| A7 | XIV | 3 | OMs | base | 198–200 | |
| A8 | XIV | 4 | OMs | HCl | 265–70 | d |
| A9 | VI | 1 | Br | FUM | >70 | d |
| A10 | XII | 1 | Br | HCl | 212–5 | |
| A11 | III | 1 | Br | HCl | 228–30 | |
| A12 | II | 1 | Br | HCl | 218–20 | |
| A13 | V | 1 | Br | HCl | 235–7 | |
| A14 | VIII | 1 | Br | base | 180–2 | |
| A15 | VII | 1 | Br | HCl | 150–60 | |
| A16 | XV | 1 | Br | HCl | 254–5 | d |
| A17 | XIV | 5 | OMs | HCl | 251–2 | |
| A18 | XIV | 6 | OMs | 2HCl | 177–80 | |
| A19 | XIV | 7 | OMs | HCl | 296–7 | d |
| A20 | XIV | 8 | Cl | HCl | 260–1 | d |
| A21 | XIV | 9 | Cl | HCl | 287–90 | d |
| A22 | XIV | 10 | Br | HCl | 290–1 | d |
| A23 | XVII | 1 | Br | HCl | 255–7 | d |
| A24 | XIII | 1 | Br | HCl | >245 | d |
| A25 | IV | 1 | Br | FUM | 90 | |
| A26 | XVI | 1 | Br | HCl | 275–9 | d |
| A27 | XVIII | 1 | Br | HCl | 243–5 | |
| A28 | XIX | 1 | Br | HCl | 183–6 | d | d = decomposition

INTERMEDIATES used in route A
  Intermediates Q–X
  Q2-OH, Q3-OH and Q5-OH to Q9-OH: Example (Q2-OH), see scheme A2: An arylboronic acid was reacted with an aromatic bromide under basic conditions in the presence of a catalytic amount of $Pd(PPh_3)_4$. This so-called "Suzuki" reaction yields the C—C coupled intermediates Q-OH. The applied boronic acids are easily accessible via the corresponding bromides, for general procedures see D. Janietz et. al., Synthesis, (1993), 33, and the references cited therein.

Procedure A2 (Scheme A2)

scheme A2

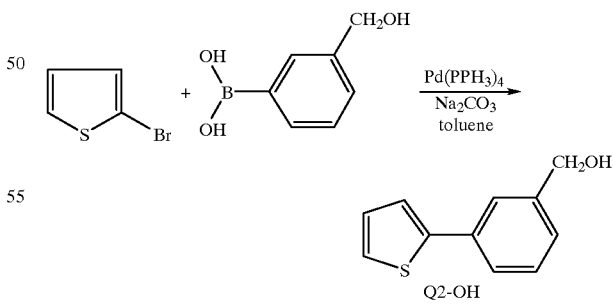

10 ml of dimethoxy-ethane was refluxed under a nitrogen atmosphere after which the solvent was allowed to cool. Subsequently 0.85 ml (1.43 g, 8.8 mmol) of 2-bromo-thiophene was added and nitrogen was bubbled through the solution for 10 minutes. Then 0.4 g (0.35 mmol, 0.04 eq) of $Pd(PPh_3)_4$ was added to the solution. After stirring for 10 minutes, 8.5 ml of 2N Na$_2$CO$_3$/H$_2$O and, secondly, 1.25 g (8.2 mmol) of 3-(hydroxymethyl)-phenyl boronic acid dissolved in circa 2 ml of EtOH, were added to the reaction mixture. The reaction mixture was heated and allowed to reflux for 4 hrs, after which the heating was discontinued, the reaction was stirred for another 16 hrs at room temperature. The formed precipitate was filtered over Celite, and the filter washed with EtOAc/H$_2$O. The filtrate was extracted with EtOAc, the combined organic fractions were dried on MgSO$_4$. After removal of the drying agent, the filtrate yielded after evaporation of the solvent 2.1 g of an oil. Flash chromatography (SiO$_2$, eluent methyl-tert.-butyl-ether/hexane 1/1) yielded 0.85 g (4.5 mmol, 51%) of the wanted product Q2-OH.

In a similar way, the following meta-substituted benzylalcohols Q-OH were made from the combinations of aromatic bromides and boronic acids given in table A2.

TABLE A2

| Q—OH | BROMIDE | BORONIC ACID |
|---|---|---|
| Q2-OH | 2-bromothiophene | 3-(hydroxymethyl)phenylboronic acid |
| Q3-OH | 3-bromothiophene | 3-(hydroxymethyl)phenylboronic acid |
| Q5-OH | 3-chloro-bromobenzene | 3-(hydroxymethyl)phenylboronic acid |
| Q6-OH | 3-methoxy-bromobenzene | 3-(hydroxymethyl)phenylboronic acid |
| Q7-OH | 3-(hydroxymethyl)-bromobenzene | 4-fluoro-phenylboronic acid |
| Q8-OH | 3-cyano-bromobenzene | 3-(hydroxymethyl)phenylboronic acid |
| Q9-OH | 2-cyano-bromobenzene | 3-(hydroxymethyl)phenylboronic acid |

All Q-OH mentioned in table A2 were successfully converted into their corresponding mesylates via standard procedures (e.g. MsCl and Et$_3$N in EtOAc). However, in the case of Q8-OH and Q9-OH, not the corresponding mesylates were obtained, but the corresponding chlorides Q8-Cl, and Q9-Cl, due to work-up with 2N HCl. The latter two were also excellent alkylating agents in the reaction depicted in scheme A1.

Intermediate Q1-Br, see scheme A3

Meta-phenyl-toluene (S$_1$=H), was subjected to bromination by the action of N-bromo-succinimide (NBS) in the presence of a catalytic amount of dibenzoylperoxide.

scheme A3

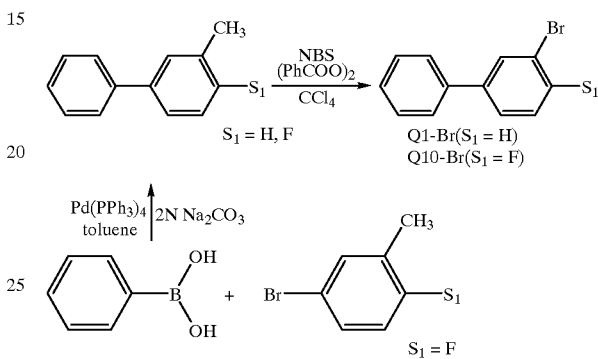

Procedure A3 (Scheme A3)

Q1-Br: 3 g (29.8 mmol) of 3-phenyl-toluene and 5.3 g (29.8 mmol) of N-bromo-succinimide (NBS) were dissolved in 30 ml of CCl$_4$. A small amount of dibenzoylperoxide was added and the reaction mixture was refluxed for 10 hrs. During this period an extra small amount of dibenzoylperoxide was added. After cooling, the reaction mixture was diluted with CCl$_4$ and water. The biphasic system was made alkaline with 2N NaOH, after which it was agitated. The organic layer was washed with 1N NaOH and water, and subsequently dried on MgSO$_4$. After removal of the drying agent the solvent was removed in vacuo leaving 8.0 g of a residue. The latter was purified by column chromatography (SiO$_2$, eluent: Et$_2$O/petroleum ether 1/9), yielding 5.3 g (21.5 mmol, 72%) of pure intermediate Q1-Br.

In the case of Q10-Br, the desired 2-fluoro-5-phenyl-toluene (S$_1$=F) was prepared from phenylboronic acid and 2-fluoro-5-bromo-toluene via a Suzuki reaction, analogously to procedure A2. See scheme A3.

Q4

Example (Q4-OH), see scheme A4

Di-methylation of 3-phenyl-4-hydroxy-benzoic acid (for preparation see U.S. Pat. No. 4,873,367) by the action of MeI/KOtBu yielded the corresponding methoxy-benzoic acid methyl ester, which on its turn could be reduced (LiAlH$_4$) to Q4-OH.

Procedure A4 (Scheme A4)

Step 1: 4.0 g (19 mmol) of 3-phenyl-4-hydroxy-benzoic acid were dissolved in 70 ml of DMF to which 4.6 g (41 mmol) of KOtBu were added, and the mixture was stirred for 30 minutes. After this period 3.0 g (21 mmol) of MeI were added and the reaction mixture was stirred for 14 hrs at room temperature, during this period a second equivalent of MeI was added. The solvent was removed in vacuo leaving a residue which was dissolved in EtOAc. The latter solution was shaken with 2N NaOH. The organic fraction was dried on $Na_2SO_4$. After removal of the drying agent and solvent, 3.65 g (16.0 mmol, 84%) of fairly pure 3-phenyl-4-methoxy-benzoic acid methyl ester was obtained. This batch was used without further purification for the reduction described in procedure A5.

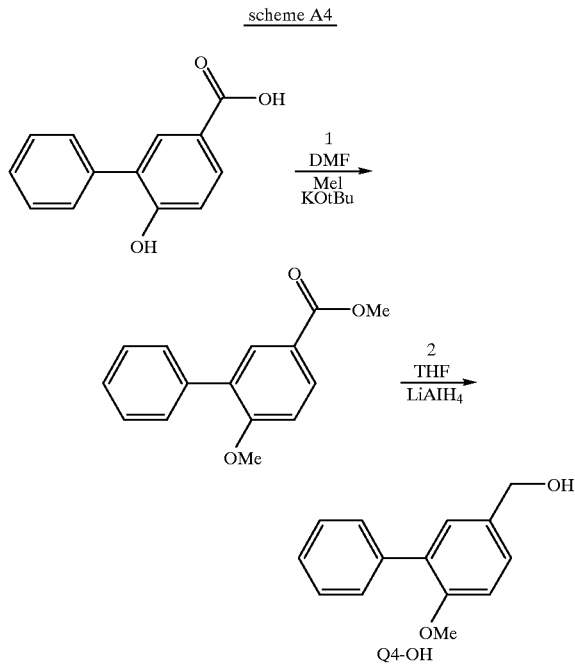

scheme A4

Procedure A5 (Scheme A4)

Step 2: 0.68 g (18 mmol) of $LiAlH_4$ were added to 20 ml of dry THF and stirred under a nitrogen atmosphere. Subsequently, 3.65 g (16.0 mmol) of 3-phenyl-4-methoxy-benzoic acid methyl ester dissolved in 60 ml of dry THF, were added dropwise to the $LiAlH_4$/THF mixture. Stirring was continued for 1 hr at room temperature. The reaction mixture was cooled (ice/water) and 0.7 ml of water mixed with THF were added, as well as 1.4 ml of 2N NaOH. Then the mixture was refluxed for 10 minutes, after which it was filtrated to remove the salts. The salts were washed with hot THF and the washings were combined with the filtrate. After removal of the solvent in vacuo 3.1 g (14.5 mmol, 90%) of fairly pure Q4-OH was obtained. This batch was used without further purification for the preparation of the mesylate Q4-OMs, which was on its turn used in the reaction depicted in scheme A1, eventually leading to the compound A8.

EXAMPLE 2

Procedure B1 (Scheme B1)

3.74 g (17.0 mmol) of piperazine I-H and 3.0 g (17.0 mmol) of 2-phenyl-phenol were dissolved in 80 ml of absolute EtOH. While stirring the solution, 2.0 ml (24.0 mmol) of 37% $CH_2O/H_2O$ was added, stirring was continued for 48 hrs. After this period the reaction mixture was concentrated in vacuo leaving a residue which was subjected to flash column chromatography ($SiO_2$, eluent $CH_2Cl_2$/petroleum ether 1/1). At first, the unreacted part of 2-phenyl-phenol was isolated, changing the eluent via 100% $CH_2Cl_2$ to $CH_2Cl_2$/MeOH 99/1, yielded 1.70 g (4.2 mmol, 25%) of compound B1 as a free base. m.p.: 174–5° C. $^1$H-NMR ($CDCl_3$, δ): 2.65(cluster, 8H), 3.83(s, 2H), 4.27(m, 4H), 6.48(dd, J=1.5 and J=8 Hz, 1H), 6.59(dd, J=1.5 and J=8 Hz, 1H), 6.76(t, J=8 Hz, 1H), 6.87(t, J=8 Hz, 1H), 7.05(dd, J=1.5 and J=8 Hz, 1H), 7.28(dd, J=1.5 and J=8 Hz, 1H), 7.32(m, 1H), 7.42(t, J=8 Hz 2H), 7.61(m, 2H), 11.4(broad s, 1H).

TABLE B

| compound nr | piperazine | Q | SALT | melting point ° C. |
|---|---|---|---|---|
| B1 | I | 11 | base | 174–5 |

EXAMPLE 3

Procedure C1 (Scheme C1)

Step 1: Under a nitrogen atmosphere, 0.8 g (3.4 mmol) of 3-(3-methoxy-phenyl)benzoic acid were dissolved in 15 ml of dry THF together with 0.65 ml of $Et_3N$. The solution was cooled to 0° C. and stirred while 0.42 ml of i-ButO(CO)Cl was added. After 30 minutes, 0.71 g (3.2 mmol) of I-H dissolved in 5 ml of dry THF were added to the former solution. The reaction mixture was allowed to reach room temperature and stirring was continued for 16 hrs. After this period the reaction mixture was treated with 2N NaOH, subsequently the biphasic system was extracted with EtOAc. The organic fraction was dried on $MgSO_4$. After removal of the drying agent and removal of the solvent in vacuo, a residue was left which was subjected to column chromatography ($SiO_2$, eluent: EtOAc/petroleumether 1/1). Yield: 0.75 g (1.7 mmol, 52%) of the corresponding amide.

Step 2: 0.9 g of $LiAlH_4$ was suspended in 20 ml of dry THF, the latter suspension was brought to reflux temperature after which 0.7 g (1.6 mmol) of the amide (product of step 1) dissolved in 15 ml of dry THF, were added to the suspension. Reflux was continued for 15 minutes, after which the reaction mixture was cooled (ice/water) and 0.9 g of $H_2O$ were added dropwise very carefully. Subsequently 1.8 ml of 2N NaOH and 0.9 g of $H_2O$ were added, after which the mixture was brought to reflux temperature again for 20 minutes. Cooling to room temperature and filtration left a residue which was washed with EtOAc. The combined filtrate and washings were dried on $MgSO_4$. After removal of the drying agent and removal of the solvent in vacuo, a residue was left which was subjected to column chromatography ($SiO_2$, eluent: EtOAc). Yield: 0.57 g (1.4 mmol, 85%) of pure free base C1. The latter was dissolved in EtOAc and transformed into its HCl salt by addition of one equivalent of 1N HCl/MeOH, yielding 0.50 g of pure C1.HCl. m.p.: 165–7 (dec.). $^1$H-NMR($CDCl_3$, δ): 3.24(broad, 2H), 3.42–3.58(cluster, 4H), 3.64–3.84(broad, 2H), 3.90(s, 3H), 4.26(m, 4H), 4.30(s, 2H), 6.67(broad d, J=8 Hz, 2H), 6.79(t, J=8 Hz, 1H), 6.93(m, 1H), 7.23(m, 2H), 7.38(t, J=8 Hz, 1H), 7.52(t, J=8 Hz, 1H), 7.65(broad d, J=8 Hz, 1H), 7.69(broad d, J=8 Hz, 1H), 7.92(broad s, 1H), 13.2(broad, 1H).

Procedure C2 (Scheme C2)

Steps 1 and 2: These reactions are analogous to procedure C1, steps 1 and 2 (scheme C1).

Step 3: 1.1 g (2.4 mmol) of the acetic acid ester were suspended in 150 ml of EtOH together with 15 ml of H$_2$O after which 1.5 g (37.5 mmol) of NaOH were added. The reaction mixture was stirred for 16 hrs after which the EtOH was removed in vacuo. The remaining fraction was treated with saturated NH$_4$Cl solution and extracted with CH$_2$Cl$_2$. The combined organic fractions were washed with saturated NaHCO$_3$ solution and dried on MgSO$_4$. After removal of the drying agent and removal of the solvent in vacuo, a residue of 0.97 g (2.3 mmol, 97%) was left containing the corresponding pure phenol derivative.

Step 4: 0.98 g (2.3 mmol) of the phenol derivative (obtained in step 3) were dissolved in 15 ml of acetone in which 1.5 g of powdered K$_2$CO$_3$ were added. While stirring, 0.3 ml of (CH$_3$)$_2$SO$_4$ was added, after which the reaction mixture was refluxed for 2 hrs. After the reaction mixture reached room temperature, the solvent was removed in vacuo. To the remaining fraction 30 ml of H$_2$O were added, subsequently the mixture was boiled for 45 minutes. After cooling of the mixture, extraction with CH$_2$Cl$_2$ took place, the organic fraction was dried on MgSO$_4$. After removal of the drying agent and removal of the solvent in vacuo, a residue of 0.95 g (2.2 mmol, 96%) of the corresponding pure O-methylated phenolic derivative was left.

The synthesis of compound C4 was similar to the one described for C2.

In table C the compounds are summarized.

TABLE C

| compound nr | piperazine | Q | SALT | melting point ° C. | |
|---|---|---|---|---|---|
| C1 | I | 6 | HCl | 165–7 | d |
| C2 | I | 12 | base | 197–8 | |
| C3 | I | 4 | HCl | >148 | d |
| C4 | XIV | 12 | HCl | 255–7 | | d = decomposition

INTERMEDIATES used in route C

Scheme C.3

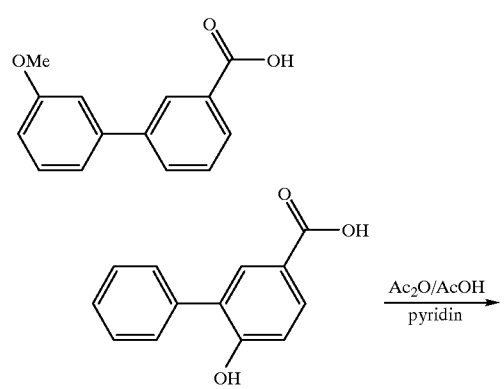

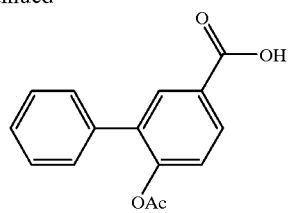

3-(3-methoxy-phenyl)-benzoic acid (scheme C3) was prepared similarly to the procedure described by W. G. Dauben et.al., J. Am. Chem. Soc., 75, (1953), 4969–73. 3-phenyl-4-acetoxy-benzoic acid (scheme C3) was prepared from 3-phenyl-4-hydroxy-benzoic acid by standard procedures, see scheme C3. The synthesis of the later compound has been described in U.S. Pat. No. 4,873,367.

EXAMPLE 4

Procedure D1 (Scheme D1)

Under a nitrogen atmosphere, 0.4 g (2.8 mmol) of 4-bromo-phenol was dissolved in 5 ml of toluene. To the latter solution, 97.5 mg (0.084 mmol, 0.03 eq.) of Pd(PPh$_3$)$_4$, 2.8 ml of 2N Na$_2$CO$_3$ and 1.0 g (2.8 mmol) of boronic acid d1 (S$_5$=H) dissolved in 5 ml of hot EtOH, were added. The resulting mixture was stirred vigorously at 90° C. for a period of 4 hrs. After the reaction mixture had reached room temperature, it was diluted with EtOAc and a little water. Then extraction with EtOAc took place, the combined organic fractions were washed with brine and dried on MgSO$_4$. After removal of the drying agent, and subsequent removal of the solvent in vacuo, 1.52 g of a residue was left which was subjected to column chromatography (SiO$_2$, eluent EtOAc/petroleum ether 1/1). Yield: 0.53 g (1.3 mmol, 47%) of the pure free base D22. The free base was converted in to its di-HCl salt (crystallization from EtOAc/ether) yielding D22.2HCl. m.p.: 222–7° C. $^1$H-NMR (d6-DMSO/CDCl$_3$ 4/1, δ): 3.14–3.30(broad cluster, 4H), 3.34–3.56 (broad cluster, 4H), 4.23(m, 4H), 4.42(d, J=4 Hz, 2H), 6.46–6.58(cluster, 2H), 6.73(t, J=8 Hz, 1H), 6.89(m, 2H), 7.47(t, J=7 Hz, 1H), 7.52–7.66(cluster, 4H), 7.99(t, J=1 Hz, 1H), 9.40(broad, O$\underline{H}$ N$^+\underline{H}$ H$_2$O), 11.5(broad, 1H).

According to the syntheses given above, the following compounds were made (table D).

TABLE D

| compound nr | piperazine | Q | SALT | melting point ° C. | |
|---|---|---|---|---|---|
| D1 | I | 9 | HCl | 185 | d |
| D2 | I | 8 | HCl | 193 | d |
| D3 | I | 16 | base | 141—3 | |
| D4 | I | 17 | base | 132–3 | |
| D5 | I | 18 | HCl | 178–80 | d |
| D6 | I | 2 | 2HCl | 199–201 | |
| D7 | I | 19 | 2HCl | 188–90 | d |
| D8 | I | 3 | 2HCl | 228–30 | |
| D9 | I | 20 | base | 177–8 | |
| D10 | I | 21 | 2HCl | 208–12 | d |
| D11 | I | 22 | 2HCl | 218–22 | |
| D12 | I | 23 | 2HCl | 216–9 | |
| D13 | I | 24 | 2HCl | >192 | d |
| D14 | I | 25 | 2HCl | >230 | d |
| D15 | I | 26 | 2HCl | >200 | d |

TABLE D-continued

| compound nr | piperazine | Q | SALT | melting point ° C. |
|---|---|---|---|---|
| D16 | I | 27 | 2HCl | 215–7 d |
| D17 | I | 28 | 2HCl | 185–91 |
| D18 | I | 29 | 2HCl | 208–12 |
| D19 | I | 30 | 2HCl | glass |
| D20 | I | 31 | 2HCl | >200 d |
| D21 | I | 32 | base | 124–5 |
| D22 | I | 33 | 2HCl | 222–7 |
| D23 | I | 34 | HCl | 234–5 | d = decomposition

INTERMEDIATES used in route D

The bromides used in scheme D1 and D2 are easily accessible by standard methods or are commercially available. The applied boronic acids in schemes D1 and D2 are easily accessible via the corresponding bromides (scheme D3), for general procedures see D. Janietz et. al., Synthesis, (1993), 33, and the references cited therein.

scheme D3

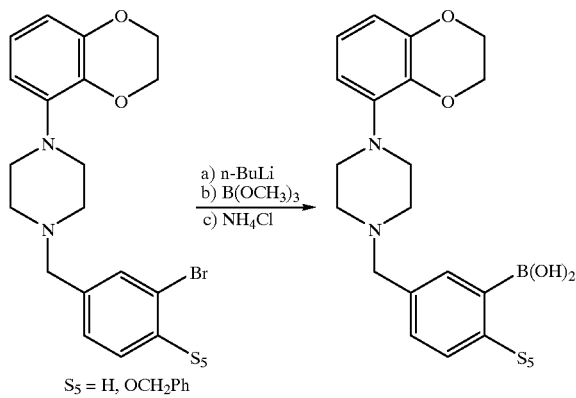

$S_5$ = H, OCH$_2$Ph

The used bromides ($S_5$=H, OCH$_2$Ph, scheme D3) are synthesized analogously to the procedure described in procedure E3 (scheme E3).

EXAMPLE 5

Procedure E1 (Scheme E1)

5.1 g (12.0 mmol) of 1-[(2-methoxy-5-bromo-phenyl) methyl]-4-(2,3-dihydro1,4-benzo dioxin-5-yl) piperazine were dissolved in 20 ml of toluene, to which 12 ml of 2N Na$_2$CO$_3$/H$_2$O and 0.45 g (0.39 mmol, 0.03 eq.) of Pd(PPh$_3$)$_4$ were added. Then 1.46 g (12.0 mmol) of phenyl-boronic acid dissolved in 3 ml of warm EtOH, were added to the solution. The reaction mixture was stirred vigorously at a temperature of 85° C. After a period of 4 hrs the biphasic reaction mixture was allowed to reach room temperature after which the organic (toluene) fraction was separated. The water layer was extracted with EtOAc. The combined toluene- and EtOAc fractions were washed with water and brine respectively, after which the organic fraction was dried on Na$_2$SO$_4$. After removal of the drying agent, and subsequent removal of the solvent in vacuo, a residue was left which was subjected to column chromatography (SiO$_2$, eluent EtOAc/petroleum ether 1/2). The isolated pure free base of E2 was dissolved in EtOAc/EtOH 1/1 and the latter solution treated with 1 equivalent of 1N HCl/EtOH. Yield: 1.43 g (3.2 mmol, 26%) of E2.HCl. m.p.: 240–2° C. (dec.).
$^1$H-NMR (d6-DMSO/CDCl$_3$ 4/1, δ): 3.1–3.3 (cluster, 4H), 3.48(cluster, 4H), 3.93(s, 3H), 4.23(m, 4H), 4.41(d, J=5 Hz, 2H), 6.48(dd, J=1 Hz, J=8 Hz, 1H), 6.55(dd, J=1 Hz, J=8 Hz, 1H), 6.73(t, J=8 Hz, 1H), 7.20(d, J=9 Hz, 1H), 7.32(m, 1H), 7.40(t, J=8 Hz, 2H), 7.71(m, 2H), 7.75(dd, J=2 Hz, J=9 Hz, 1H), 8.04(d, J=2 Hz, 1H), 11.1(broad, 1H).

Procedure E2 (Scheme E2)

3.0 g (5.9 mmol) of O-benzyl protected compound E1 were dissolved in 35 ml of concentrated HCl after which the mixture was stirred and brought to reflux temperature. After a period of 45 minutes an extra amount of 30 ml of concentrated HCl was added and refluxing was continued for another 45 minutes. After this period, the reaction mixture was allowed to reach room temperature and the solvent was removed in vacuo. The residue was treated with saturated NaHCO$_3$ solution and the latter extracted with EtOAc. The organic fraction was washed with brine and subsequently dried on MgSO$_4$. After removal of the drying agent, and subsequent removal of the solvent in vacuo, a residue was left which was subjected to flash column chromatography (SiO$_2$, eluent CH$_2$Cl$_2$/MeOH 95/5). The free base of E1 was isolated and converted into its HCl salt by treatment with 1N HCl/EtOH. Recrystallization from EtOH/H$_2$O yielded 1.45 g (3.2 mmol, 54%) of pure E1.HCl.

The compounds mentioned above are summarized in table E.

TABLE E

| compound nr | piperazine | Q | SALT | melting point ° C. |
|---|---|---|---|---|
| E1 | I | 13 | HCl | >190 d |
| E2 | I | 14 | HCl | 240–2 d |
| E3 | XIV | 15 | HCl | 271–3 d | d = decomposition

INTERMEDIATES used in route E

The bromides used for the Suzuki reaction depicted in scheme E1 can be synthesized from phenyl-piperazines and the desired substituted 3-bromo-phenyl-methyl-X intermediates in which X may represent Cl, Br or OMs (see scheme E3).

scheme E3

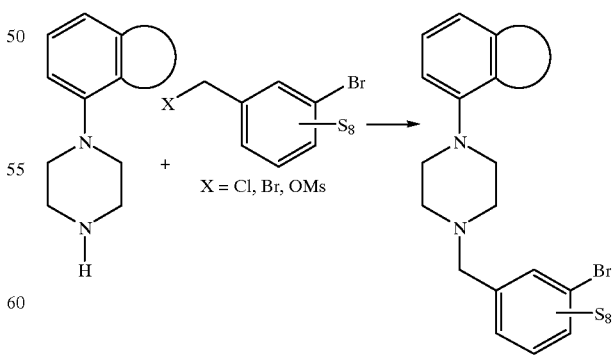

X = Cl, Br, OMs

Procedure E3 (scheme E3)

6.6 g (23.0 mmol) of (2-methoxy-5-bromo-phenyl)-methyl-bromide and 5.4 g (21 mmol) of I-H.HCl were added to 80 ml of CH₃CN after which 5.2 g (51.0 mmol) of Et₃N and a small amount of KI were added. The reaction mixture was stirred and kept at reflux temperature for 16 hrs. After this period the reaction mixture was filtered and the filtrate was concentrated in vacuo. The residue was subjected to column chromatography (SiO₂, eluent EtOAc/petroleum ether 1/2), eventually leading to 5.1 g (12.2 mmol, 58%) of pure 1-[(2-methoxy-5-bromo-phenyl)methyl]-4-(2,3-dihydro-1,4-benzodioxin-5-yl) piperazine.

The applied boronic acids are easily accessible via the corresponding bromides, for general procedures see D. Janietz et. al., Synthesis, (1993), 33, and the references cited therein.

Preparation of intermediate XI-H according to scheme A.i

Step 1 (scheme A.i)

5.1 g (25 mmol) of 1-(phenylmethyl)-hexahydro-5H-1,4-di-azepin-5-one (for preparation see Dickerman et. al., J. Org. Chem., 19, (1954), 1855–61) and 7.39 g (37.5 mmol) of 7-bromobenzfurane together with 3.45 g (25 mmol) of dried K₂CO₃ and 0.48 g (2.5 mmol) of CuI were put together in a flask and heated at 120° C. for 90 hrs while the mixture was stirred. After the reaction mixture was brought to room temperature, 40 ml of toluene were added. The latter suspension was filtered over Celite, the residue washed with warm toluene. The combined washings and filtrate were evaporated in vacuo leaving 12.4 g of a brown oil. The latter was diluted with CH₂Cl₂ and treated respectively with 2N NaOH, NaHCO₃(sat.) and water. The organic fraction was dried on MgSO₄. After removal of the drying agent and evaporation of the solvent in vacuo, 11.7 g of a brown oil was left. The latter residue was subjected to flash column chromatography (SiO₂, eluent: CH₂Cl₂/MeOH 98/2) and yielded 5.7 g (83%) of desired product.

Step 2 (scheme A.i)

5.9 g (18.6 mmol) of the product of step 1 dissolved in 40 ml of dry THF was added dropwise to a mixture of 2.14 g (55.8 mmol) LiAlH₄ in 100 ml of Et₂O, stirring was continued for 3 hrs. After this period the reaction mixture was treated with respectively 2.1 ml of H₂O in THF, 4.2 ml of 2N NaOH and 2.4 ml of H₂O. Stirring was continued for 2 hrs, after which the mixture was filtered over Celite, the residue washed with THF and CH₂Cl₂ respectively. The combined washings and filtrate were evaporated in vacuo leaving 5.4 g of a brown oil. The latter residue was subjected to flash column chromatography (SiO₂, eluent: CH₂Cl₂/MeOH 98/1) and yielded 4.83 g (85%) of the diazepine analog.

Step 3 (scheme A.i)

4.83 g (15.8 mmol) of the product of step 2 was dissolved in 65 ml of 1,2-dichloroethane while stirring. Under a nitrogen atmosphere, at 2–4° C., 2.3 g (15.8 mmol) of Cl(CO)O(CHCl)CH3 ("ACE-chloride") dissolved in 25 ml of 1,2-dichloroethane, was added dropwise to the former solution in a 10 minute period. Then the reaction mixture was refluxed for 10 hrs. After this period the reaction mixture was concentrated in vacuo to leave 5.1 g of a residue. The latter was diluted with MeOH and the obtained solution was refluxed for 16 hrs. After the reaction mixture was brought to room temperature, the solvent was removed in vacuo to leave 4.2 g of a residue which was subjected to flash column chromatography (SiO₂, eluent: CH₂Cl₂/MeOH/NH₄OH 92/7.5/0.5). Yield: 2.8 g (82%) of 1-(7-benzfuranyl)-hexa-hydro-1,4-diazepine.

Preparation XV-H, see scheme A.iii

Step 1 (scheme A.iii)

3.94 g (21.9 mmol) of 7-nitro-2-benzoxazolinone (for preparation of the latter compound, and European patent EPO189612 and references cited therein) were dissolved in 40 ml of DMSO after which 1.72 g of 85% powdered KOH (26.2 mmol) were added. While stirring and cooling (water) 3.72 g (26.2 mmol) of MeI dissolved in 6 ml of DMSO, were added dropwise over a period of 10 minutes. Stirring was continued at room temperature for 16 hrs, during the latter period an extra amount of MeI (0.5 g) was added. After the reaction was completed, the reaction mixture was diluted with water after which extraction took place with CH₂Cl₂. The combined organic fractions were washed with respectively water and brine after which the organic fraction was dried on MgSO4. After removal of the drying agent and evaporation of the solvent in vacuo, 4.1 g of a solid residue was left. Flash column chromatography (SiO₂, eluent: CH₂Cl₂) of the latter yielded 3.6 g (85%) of pure 3-methyl-7-nitro-2-benzoxazolinone.

What is claimed is:

1. A compound having the formula (a)

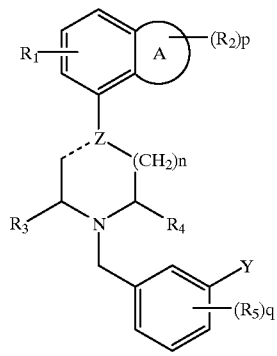

wherein

A represents a heterocyclic group having 5–7 ring atoms in which 1–3 heteroatoms selected from the group O, N and S are present, $R_1$ is hydrogen or fluoro, $R_2$ is $C_{1-4}$-alkyl, $C_{-1-4}$-alkoxy or an oxo group, and p is 0, 1 or 2, Z represents nitrogen, and the dotted line represents a single bond, $R_3$ and $R_4$ independently are hydrogen or $C_{1-4}$-alkyl, n has the value 1, $R_5$ is halogen, hydroxy, $C_{1-4}$-alkoxy or $C_{1-4}$-alkyl, and q is 0, 1, 2 or 3, Y is a phenyl, furanyl or thienyl group, which groups may be unsubstituted or substituted with 1–3 substituents selected from hydroxy, halogen, $C_{1-4}$-alkoxy, $C_{1-4}$-alkyl, cyano, aminocarbonyl, mono- and di-$C_{1-4}$-alkylaminocarbonyl, or a pharmacologically acceptable salt thereof.

2. A compound according to claim 1, wherein A together with the phenyl group represents a group selected from the groups having formulae (b)–(m)

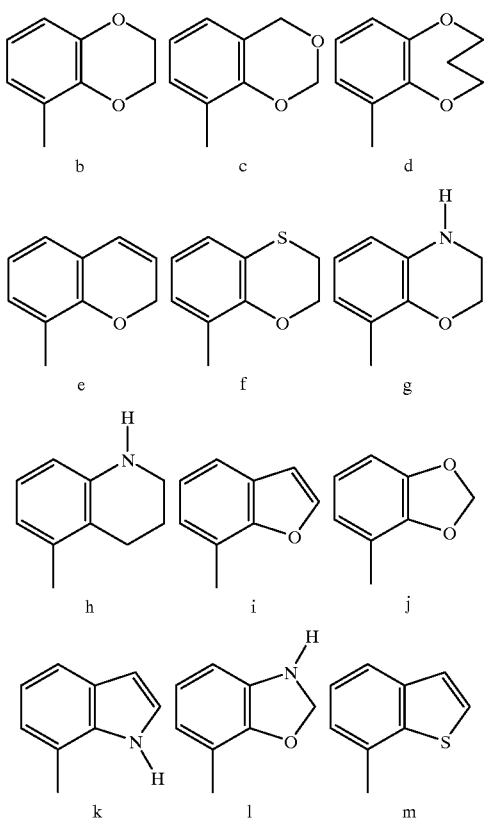

wherein

R₁ and (R₂)p have the meanings given in claim 1, n is 1, and R₃, R₄, (R₅)$_q$, Y and Z have the meanings given in claim 1, or a pharmacologically acceptable salt thereof.

3. A compound according to claim 2, wherein A together with the phenyl group represents a group of the formula (b), or a group of the formula (I) which is substituted in the hetero ring with an oxo group, Y is phenyl which may be unsubstituted or substituted with 1–3 substituents selected from hydroxy, halogen, $C_{1-4}$-alkoxy, $C_{1-4}$-alkyl, cyano, aminocarbonyl, mono- and di-$C_{1-4}$-alkylaminocarbonyl, and Z is nitrogen, or a pharmacologically acceptable salt thereof.

4. A compound according to claim 3, wherein R₃ and R₄ are hydrogen, q is 0 or hydroxy, methoxy or halogen, and Y is phenyl which may be unsubstituted or substituted with 1–3 substituents selected from hydroxy, halogen, $C_{1-4}$-alkoxy, $C_{1-4}$-alkyl, cyano, aminocarbonyl, mono- and di-$C_{1-4}$-alkylaminocarbonyl, or a pharmacologically acceptable salt thereof.

5. A compound according to claim 4, wherein A together with the phenyl group is a group of formula (I) which is substituted in the hetero ring with an oxo group, q is 0, and Y is phenyl, or a pharmacologically acceptable salt thereof.

6. A method for preparing a compound of the formula (a) according to claim 1, which method comprises a) reacting a compound of the formula (n):

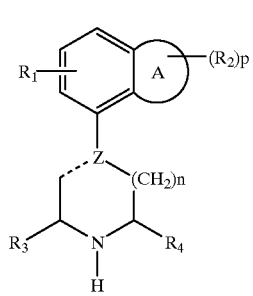

with a compound of the formula

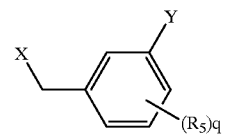

wherein X is a leaving group; or b) reacting a compound of the formula (n) with a compound of the formula

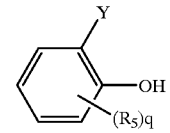

and formaldehyde; or c) reacting a compound of formula (n) with a compound of the formula

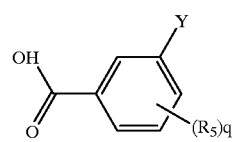

and subsequently reducing the keto-group of said reaction product; or d) reacting a compound of the formula

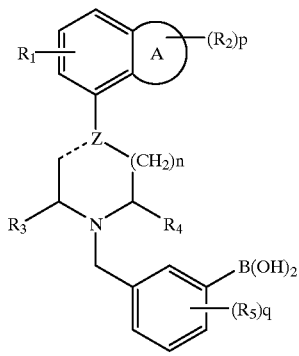

with a compound Y-Br; or e) reacting a compound of the formula

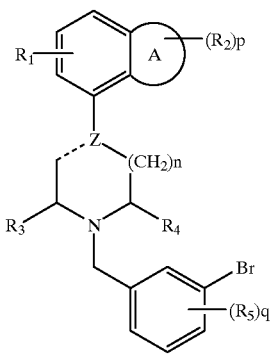

with a compound of the formula

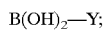

wherein $R_1$, $R_2$, $R_3$, $R_4$, $R_5$, Z, A, p, q, n and Y have the meanings given in claim 1.

7. A pharmaceutical composition, said composition comprising a pharmaceutically effective amount of at least one compound of the formula (a) according to claim 1 or a pharmacologically acceptable salt thereof, and a pharmaceutically acceptable carrier.

8. A method for preparing a pharmaceutical composition for treating a CNS disorder, said method comprising combining a pharmaceutically effective amount of at least one compound of the formula (a) according to claim 1 or a pharmacologically acceptable salt thereof and a pharmaceutically acceptable carrier.

9. A method for treating a CNS disorder, said method comprising administering to a host in need of said treatment an effective amount of a compound of formula (a) according to claim 1 or a pharmacologically acceptable salt thereof.

10. A method for treating schizophrenia or a psychotic disorder, said method comprising administering to a host in need of said treatment an effective amount of a compound of formula (a) according to claim 1 or a pharmacologically acceptable salt thereof.

* * * * *

UNITED STATES PATENT AND TRADEMARK OFFICE
CERTIFICATE OF CORRECTION

PATENT NO. : 6,225,312 B1  
DATED : May 1, 2001  
INVENTOR(S) : Feenstra et al.

Page 1 of 1

It is certified that error appears in the above-identified patent and that said Letters Patent is hereby corrected as shown below:

<u>Claim 4, column 29,</u>  
Line 53, after "q is O or", insert -- $R_5$ is --.

Signed and Sealed this

Thirtieth Day of October, 2001

Attest:

NICHOLAS P. GODICI  
Acting Director of the United States Patent and Trademark Office

*Attesting Officer*